United States Patent
Romero

(10) Patent No.: US 7,884,602 B2
(45) Date of Patent: Feb. 8, 2011

(54) NUCLEAR MAGNETIC RESONANCE EVALUATION USING INDEPENDENT COMPONENT ANALYSIS (ICA)-BASED BLIND SOURCE SEPARATION

(75) Inventor: Pedro Antonio Romero, Buenos Aires (AR)

(73) Assignee: Baker Hughes Incorporated, Houston, TX (US)

( * ) Notice: Subject to any disclaimer, the term of this patent is extended or adjusted under 35 U.S.C. 154(b) by 156 days.

(21) Appl. No.: 11/901,937

(22) Filed: Sep. 18, 2007

(65) Prior Publication Data

US 2009/0072824 A1    Mar. 19, 2009

(51) Int. Cl.
G01V 3/00    (2006.01)
(52) U.S. Cl. ..................................................... 324/303
(58) Field of Classification Search .......... 324/300–322
See application file for complete search history.

(56) References Cited

U.S. PATENT DOCUMENTS 6,711,528 B2 *   3/2004   Dishman et al. ............ 702/189
6,954,066 B2 *   10/2005  Siess et al. ................. 324/303
2005/0231198 A1 * 10/2005  Beard et al. ................ 324/303

* cited by examiner

*Primary Examiner*—Melissa J Koval
*Assistant Examiner*—Dixomara Vargas
(74) *Attorney, Agent, or Firm*—Mossman Kumar & Tyler PC

(57) ABSTRACT

Disclosed is a non-lineal statistical independent component (ICA) analysis methodology for calculating T2 or T1 distributions of nuclear magnetic resonance logs. In one aspect, the invention employs a classical blind source separation (BSS) approach with the input data (T2 or T1 distributions) being considered not only horizontally (in relaxation time units), but also vertically (in depth). The statistical variations are used for separating the principal independent components and their corresponding weighting matrix. The result of such ICA based BSS is an efficient separation of T2 components correlative to the presence of particular conditions (e.g., clay bound water, heavy oil, capillary bound water, free water, mud filtrate (water and oil), and noise). Individual saturation of estimated fluids can be calculated from the weighting matrix generated in accordance with the invention. In accordance with a further feature of the invention, it is contemplated that independent component analysis techniques may be applied to the underlying time domain data prior to its transformation to a T2 distribution. This advantageously results in "de-noising" of the signal, leading to more precise and accurate results following analysis of the T2 distribution.

6 Claims, 10 Drawing Sheets

NUCLEAR MAGNETIC RESONANCE EVALUATION USING INDEPENDENT COMPONENT ANALYSIS (ICA)-BASED BLIND SOURCE SEPARATION

FIELD OF THE INVENTION

The present invention relates generally to the analysis of data associated with subsurface exploration regions, and more particularly relates to the processing of nuclear magnetic resonance (NMR) or similar data.

BACKGROUND OF THE INVENTION

The measurement of the nuclear magnetic properties of a subterranean formation, and in particular, the quantification of certain properties resulting from or indicative of the presence or absence of hydrogen atoms (and hence, the presence or absence of hydrocarbons), is commonly practiced in the art. The basic core and log NMR measurements, and in particular those commonly referred to as T2 decay measurements, may be presented as a distribution of T2 amplitudes versus time at each of one or more sample depths.

It is widely known among practitioners of NMR exploration projects that T2 decay data may be further processed to derive total pore volume values (the total porosity) and pore volumes within different ranges of T2. The most common volumes are bound fluid and free fluid. A permeability estimate can be derived from T2 distribution data using a transform such as the Timur-Coates transform and/or the SDR permeability transform, among many others known to those of ordinary skill in the art. By running the log with different acquisition parameters, direct hydrocarbon typing and enhanced diffusion are possible.

NMR exploration methodologies are based upon the fact that the nuclei of many elements (and in particular, hydrogen) have angular momentum (spin) and a magnetic moment. The nuclei have a characteristic frequency of oscillation, known to those of ordinary skill in the art as the Larmor frequency, which is related to the magnitude of the magnetic field in their locality.

In typical implementations, there are two phases to NMR measurement: polarization and acquisition. First, the nuclear spins of nuclei in the exploration region are brought into alignment (polarized) by means of introducing a static magnetic field (BO), resulting in a net magnetization. The nuclear polarization takes a characteristic time T1 to achieve equilibrium. Second, the equilibrium state is disrupted or "tipped" by a burst from an oscillating magnetic field. The oscillating magnetic field is designed to tip the nuclear spins with resonant frequency within the bandwidth of the oscillating magnetic field away from the static field direction. After tipping, the spins precess around the static field at a particular frequency known as the Larmor frequency.

At the end of a "tipping" pulse, spins on resonance are pointed in a common direction, and they precess at the Larmor frequency. However, due to such factors as inhomogeneity in the static field, imperfect instrumentation, or microscopic material inhomogeneities, each nuclear spin precesses at a slightly different rate than the others. Thus, after time, the spins will no longer be precessing in phase with one another. This "dephasing" as it is known can be accounted for using known techniques, for example, generating spin "echoes" by applying a series of pulses to repeatedly refocus the spin system. The decay (time constant) of echo amplitude correlates in known fashion by properties of the material being explored, and is commonly quantified as a so-called T2 relaxation value.

Furthermore, it has been shown that echo amplitude decay is composed of a plurality of different decay components, forming what is known as a "T2 distribution."

The foregoing description of polarization and acquisition phases of a NMR study provides a summary of concepts (such as T2 distributions and the Larmor frequency) and processes (such as data transforms) that, while complex and likely beyond the scope of a hypothetical average person's knowledge or familiarity, would be understood and well within the range of expertise of a person of ordinary skill in this particular art.

Those of ordinary skill in the art will be also be aware that the well-known CPMG cycle of radio frequency pulses designed by Carr, Purcell, Meiboom and Gill may be used to produce echo trains appropriate for NMR measurements.

In a standard CPMG sequence, an initial electromagnetic (typically radio frequency) pulse is applied long enough to "tip" the protons into a plane perpendicular to the static magnetic field (the 90° pulse). Initially the protons precess in unison, producing a large signal in the antenna, but then quickly dephase due to the inhomogeneities. Another pulse is applied, long enough to reverse their direction of precession (the 180° pulse), and causing them to come back in phase again after a short time. Being in phase, they produce another strong signal called an echo. They quickly dephase again but can be rephased by another 180° pulse. Rephasing may be (and customarily is) repeated many times, while measuring the magnitude of each echo. The echo magnitude decreases with time due to the molecular relaxation mechanism's surface, bulk, and diffusion, among other factors. One "measurement" typically may comprise many hundreds of echoes in a so-called echo train, where the time between each echo (the echo spacing TE) is of the order of 1 ms or less.

NMR measurements made by both laboratory instruments and logging tools follow the same principles very closely. An important feature of NMR measurement is the time needed to acquire it. In the laboratory, time presents no difficulty. In practice, there is a trade-off between the time needed for polarization and acquisition, logging speed and frequency of sampling. The longer the polarization and acquisition, the more complete the measurement. However, the longer times require either lower logging speed or less frequent samples.

In the prior art, an NMR log analysis has been performed on a deterministic basis, which is based on the fundamental equations governing the NMR relaxation process. Although this is an acceptable approach, there is a perceived drawback in that it requires reliable, a priori knowledge of the NMR properties of the fluids in the formation, to be used as constraints in the inversion algorithms used for calculating T2 relaxation distributions.

SUMMARY OF THE INVENTION

In view of the foregoing, the methodology of the present invention is based in an illustrative embodiment on the use of non-linear statistics to perform an independent T2 (or T1 or diffusivity) component analysis (ICA) of NMR data. As would be known to ordinary skill in the art, ICA, is a statistical technique that represents a multidimensional random vector as a linear combination of nongaussian random variables ("independent components") that are as independent as possible. ICA is a nongaussian version of factor analysis, and somewhat similar to principal component analysis. ICA is known to have many applications in data analysis, source separation, and feature extraction.

In accordance with one aspect of the invention, the approach follows classical blind source separation (BSS) principles. The input data, T2 or T1 distributions, are obtained from the time domain data, received by an antenna, and are considered not only horizontally (in relaxation time units) but also vertically (in depth), and their statistical variations are used for separating their principal independent components and their corresponding weighting matrix.

In one embodiment, NMR analysis performed in accordance with the present invention is highly efficient and effective in separating T2 components corresponding to clay-bound water, heavy oil, capillary-bound water, free water, mud filtrate (water or oil), and even noise. The individual saturation of the estimated fluids can be calculated from the weighting matrix generated by the ICA algorithm.

In accordance with a further feature of the invention, ICA techniques can be applied to the underlying time-domain data to further "de-noise" the signal prior to transformation of the time-domain signal into a T2 distribution curve.

BRIEF DESCRIPTION OF THE DRAWINGS

The foregoing and other features and aspects of the present invention will be best appreciated by reference to a detailed description of the specific embodiments of the invention, when read in conjunction with the accompanying drawings, wherein:

FIG. 4d is a plot of porosity characteristics corresponding to the T2 distribution of FIG. 4a;

DETAILED DESCRIPTION OF A SPECIFIC EMBODIMENT OF THE INVENTION

In the disclosure that follows, in the interest of clarity, not all features of actual implementations are described. It will of course be appreciated that in the development of any such actual implementation, as in any such project, numerous engineering and technical decisions must be made to achieve the developers' specific goals and subgoals (e.g., compliance with system and technical constraints), which will vary from one implementation to another. Moreover, attention will necessarily be paid to proper engineering and programming practices for the environment in question. It will be appreciated that such development efforts might be complex and time-consuming, outside the knowledge base of typical laymen, but would nevertheless be a routine undertaking for those of ordinary skill in the relevant fields.

As noted above, the present invention in its presently preferred embodiment involves independent component analysis based upon principles of blind source separation (BSS) estimation. BSS can be described with reference at first to FIG. 1.

Figure 1:
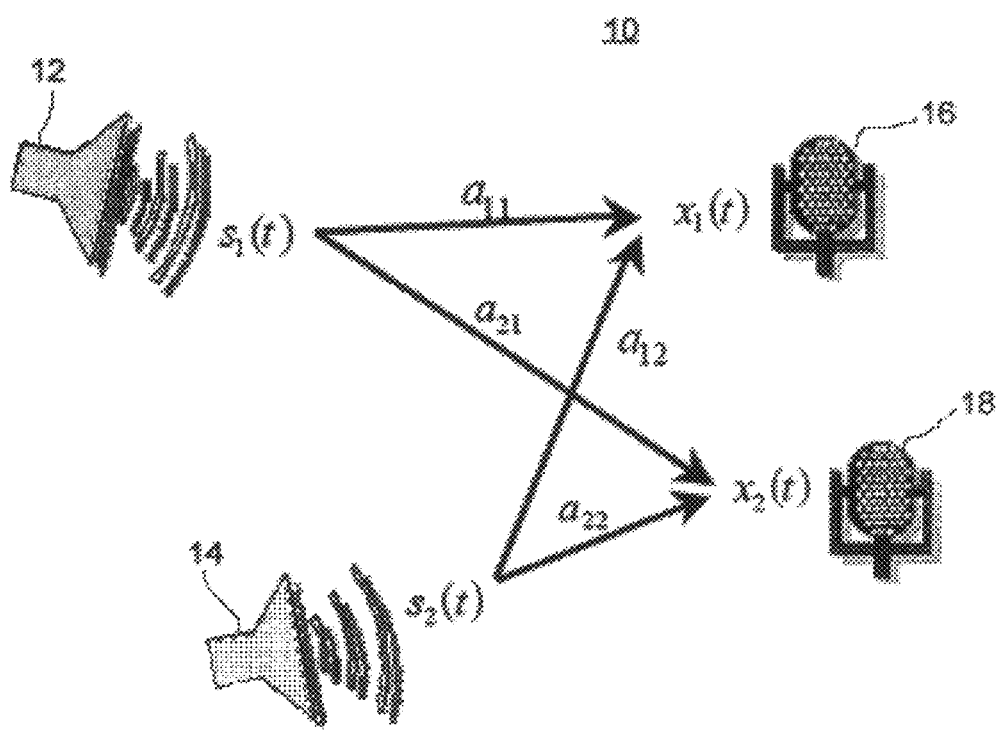
FIG. 1 is a schematic representation of a generalized multi-source nuclear magnetic resonance (NMR) system.

FIG. 1 diagrammatically depicts a hypothetical system 10 including individual sources 12 and 14 and individual detectors 16 and 18, respectively. FIG. 1 illustrates how different source signals $s_1(t)$ and $s_2(t)$ from electromagnetic pulse generators 12, 14 are recorded by detectors (sensors) 16, 18, respectively, as received signals $x_1(t)$ and $x_2(t)$. As shown in FIG. 1, a portion of source signal $s_1(t)$ is detected by receiver 16 as an observed signal $a_{11}(t)$, and another portion of source signal $s_1(t)$ is detected by sensor 18 as an observed signal $a_{21}(t)$. Likewise, a portion of source signal $s_2(t)$ is detected by receiver 16 as an observed signal $a_{12}(t)$, and another portion of source signal $s_2(t)$ is detected by sensor 18 as an observed signal $a_{22}(t)$. This results in the following expressions for $x_1(t)$ and $x_2(t)$:

$$x_1(t) = a_{11}s_1(t) + a_{12}s_2(t)$$

and $$x_2(t) = a_{21}s_1(t) a_{22}s_2(t).$$

Under the following general (not necessarily restrictive) assumptions for the linear mixing model well-known to those in the art (Comon, 1994; Cardoso and Laheld, 1996):

1. The number of sensors is greater than or equal to the number of sources.
2. The sources s(t) are at each time instant mutually independent.
3. At most one source is normally distributed.
4. No sensor noise or only low additive noise is recognized.
5. Any time delays or other extra factors from the simple mixing model are ignored.

As is known, the independent components $s_1$ and $s_2$ of the mixed signals $x_1$ and $x_2$ can be extracted using Principal Component Analysis (PCA) or Independent Component Analysis (ICA) approaches. As would be known to those of ordinary skill, a PCA approach generates orthogonal components, but not independent ones, making PCA less useful for blind source separation and denoising.

Figure 2A:
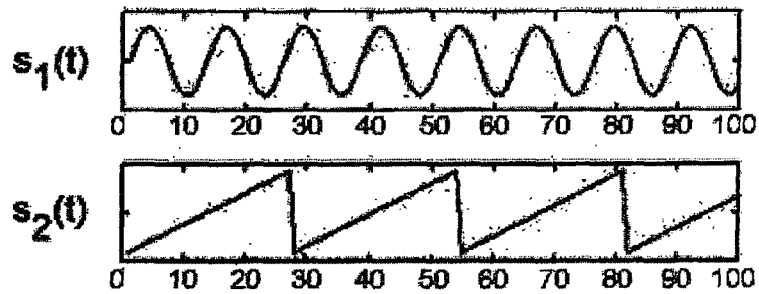
FIG. 2a shows plots of original source signals s1($t$) and s2($t$) generated by the EMF sources from FIG. 1.
Figure 2B:
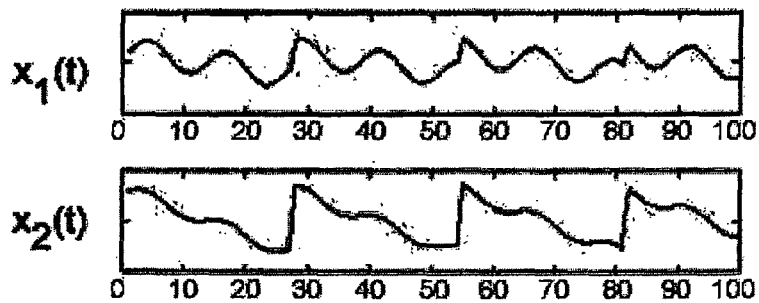
FIG. 2b shows plots of observed mixed signals x1($t$) and x2($t$) received by the sensors from FIG. 1.
Figure 2C:
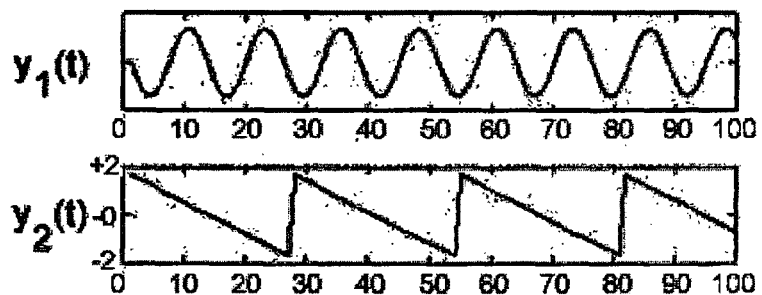
FIG. 2c shows plots of estimated source signals y1($t$) and y2($t$) derived in accordance with one embodiment of the invention.

General results after applying ICA are shown in FIGS. 2a through 2c, which show how individual signals are recorded in time by two different sensors and how the de-mixing by ICA yields the source signals. In particular, FIG. 2a shows hypothetical source signals $s_i(t)$, $s_2(t)$ from sources 12 and 14, (being a sinusoidal wave and a sawtooth wave, respectively). FIG. 2b shows observed mixed signals $x_1(t)$, $x_2(t)$, defined above. FIG. 2c shows the estimation of the source signals attainable through the practice of an ICA approach as described herein.

Those of ordinary skill in the art will appreciate that the ICA approach is more general than the PCA approach. Accordingly, and as will be hereinafter disclosed in further detail, the present invention is directed to a method of applying independent component analysis of NMR signals (echo trains in time domain or T1 or T2 distributions in T1, T2 domain).

A general understanding of independent component analysis can be appreciated from the following, in a generalized model including a plurality n of linear mixtures $x_1, x_2, \ldots x_n$, resulting from a corresponding plurality n of independent source components $s_1, s_2, \ldots s_n$, where $$x_j = a_{j1}s_1 + a_{j2}s_2 + \ldots + a_{jn}s_n = \sum_{k=1}^{n} a_{jk}s_k; \text{ for all } j$$

$x_1, x_2, \ldots x_n$ and $s_1, s_2, s_n$ are considered random, not proper time signals. The values of the signals are considered samples (instantiations) of the random variables, not functions of time. The mean value is taken as zero, without loss of generality.

Expressed in vector matrix notation, the observable variable vector x is expressed as $$x = [x_1, x_2, \ldots x_n]^T = \begin{bmatrix} x_1 \\ x_2 \\ \vdots \\ x_n \end{bmatrix}$$

and the source variables vector s is expressed as $$s = [s_1, s_2, \ldots s_n]^T = \begin{bmatrix} s_1 \\ s_2 \\ \vdots \\ s_n \end{bmatrix}$$

The mixing matrix A, then, is $$A = [a_{ij} \mid i = 1, n; j = 1, n] = [a_j \mid j = 1, n]$$

$$= \begin{bmatrix} a_{11} & \cdots & a_{1j} & \cdots & a_{1n} \\ \vdots & & \vdots & & \vdots \\ a_{i1} & \cdots & a_{ij} & \cdots & a_{in} \\ \vdots & & \vdots & & \vdots \\ a_{n1} & \cdots & a_{nj} & \cdots & a_{nn} \end{bmatrix}$$

The linear mixing equation, i.e., the independent component analysis (ICA) model is elegantly reduced to:

$$x = A*s$$

Denoting by $a_j$, the $j^{th}$ column of matrix A the model thus becomes:

$$x = \sum_{i=1}^{n} a_i s_i$$

Those of ordinary skill in the art will recognize that the ICA model is a generative model, i.e., it describes how the observed data are generated by mixing the components $s_i$. The independent components are latent variables, i.e., they are not directly observable. The mixing matrix A is also unknown. Only the random vector x can be observed, and it is therefore necessary to estimate both A and s. This is preferably done under the most general possible assumptions.

Those of ordinary skill will appreciate that ICA is a special case of the so-called "blind source separation" (BSS) methodology. The term "blind" reflects the fact that very little, if anything, is known in the mixing matrix A, and few assumptions are made with respect to the source signals.

The basic assumption under ICA is that the source components are statistically independent, and hence have unknown distributions as non-Gaussian as possible, to optimize a certain contrast function. The challenge is finding the best W, where W is the unmixing matrix that gives $$y = Wx$$

which is the best estimate of the independent source vector.

If the unknown mixing matrix A is square and non-singular, then $$W = A^{-1} \text{ and } s = y$$

Otherwise, the best unmixing matrix that separates the sources as independent as possible is given by the generalized inverse Penrose-Moore matrix $$W = A^+ \text{ and } \|s - y\| = \min$$

Those of ordinary skill will recognize that there are certain ambiguities in the ICA model. For instance, the variances (energies) of the sources cannot be determined, because both A and s are unknown, and any scalar multiplier in one of the sources $s_i$ could always be canceled by dividing the corresponding column $a_i$ of A by the same scalar.

The solution to this involves "whitening" or "sphering" of the independent components, i.e., selecting all variances equal to one:

$$E\{s_i^2\} = 1$$

This establishes equal "magnitudes" of the sources, but the ambiguity of the sign remains, as it is possible to multiply any source by −1 without affecting the model. However, this is insignificant in most cases.

Another ambiguity in the ICA model is that the order of the sources is not known. The order of the sources in s and of the corresponding columns in A can be freely changed. For P, a permutation matrix, $$x = As = AP^{-1}Ps = A's', A' = AP^{-1}, s' = Ps$$

The solution to this ambiguity is to identify the sources using a priori knowledge about their features.

Regarding the independence of the variables, let $y_1$ and $y_2$ be two scalar-valued random variables. The variables are said to be independent if information on the value of $y_1$ does not give any information on the value of $y_2$, and vice versa. In the ICA model, this is the case for the sources $s_1$ and S2, but not for the mixture variables $x_1$ and $x_2$.

In accordance with one aspect of the invention, it has been shown that employing ICA in the processing of NMR data offers significant advantages over the prior art. In particular, it has been demonstrated that ICA-based NMR analysis facilitates the denoising of NMR echo trains, and facilitates the extraction of independent components of the T2 distributions.

Advantageously, and in accordance with one aspect of the invention, ICA methodologies can separate noise from the original signal, and can be used on the time-domain NMR signals (echo trains) resulting from a generating source signal, s(t).

Figure 3:
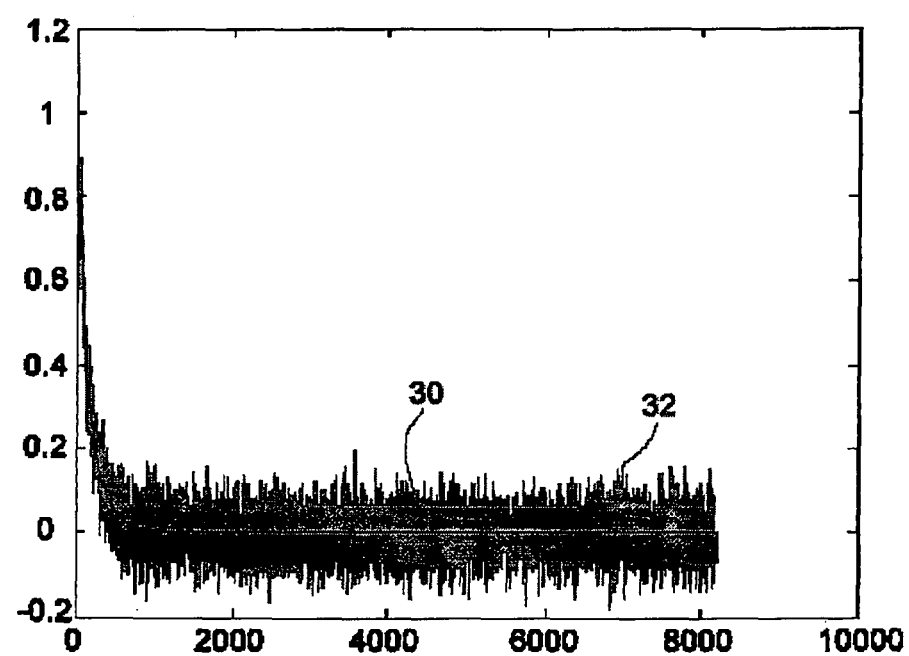
FIG. 3 shows plots of typical noisy and noise-free echo trains produced in the course of typical NMR well logging.

FIG. 3 is a plot of a noise-free (ideal) echo train 30 as received by an NMR receiver, and, superimposed therewith, a "noisy" echo train 32 exemplary of practical circumstances. In the illustrative embodiment, the noise in noisy echo train 32 is Gaussian, with sigma=0.5. (The porosity is normalized).

Figure 4A:
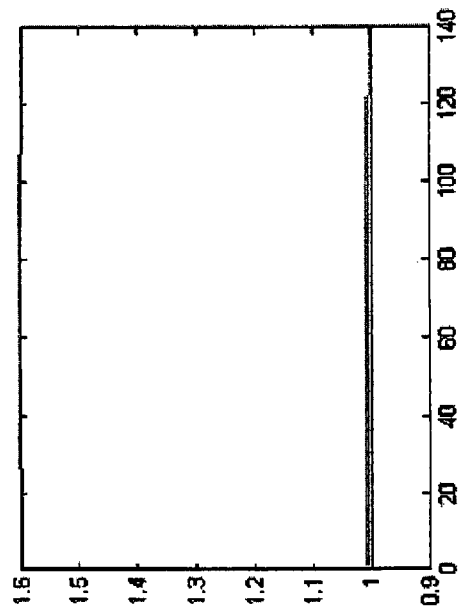
FIG. 4a is a plot of a T2 distribution curve corresponding to the noise-free echo train from FIG. 3.
Figure 4B:
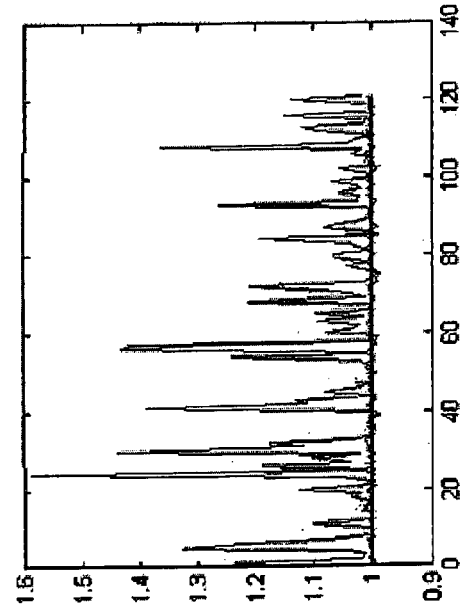
FIG. 4b is a plot of a T2 distribution curve corresponding to the noisy echo train from FIG. 3 using prior art NMR analysis techniques.

FIG. 4a is a plot of a spectral component distribution curve corresponding to a noise-less T2 distribution derived from the noise-less echo train 30 of FIG. 3. On the other hand, FIG. 4b shows a spectral component distribution curve corresponding to (derived from) noisy echo train 32 of FIG. 3, where conventional (i.e., deterministic, prior art) techniques have been applied. Finally, and notably, FIG. 4c shows a T2 distribution corresponding to (derived from) noisy echo train 32, where instead the ICA methodology of the present invention has been employed.

Figure 4D:
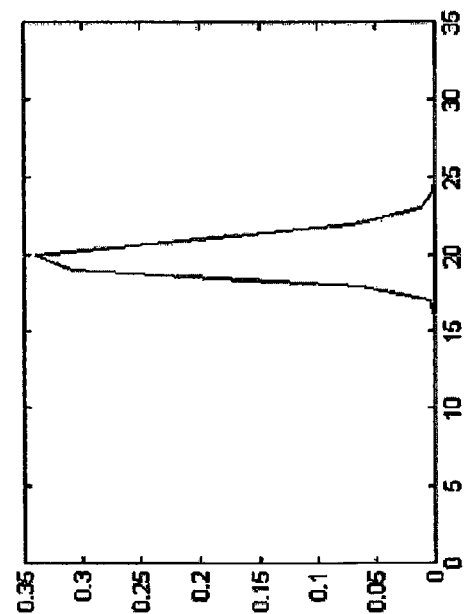
Figure 4E:
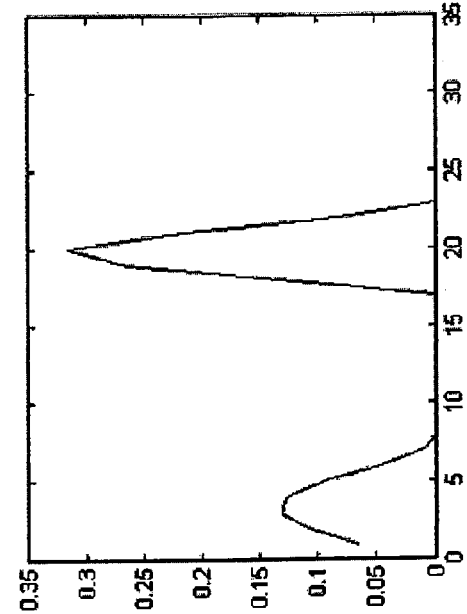
FIG. 4e is a plot of porosity characteristics corresponding to the T2 distribution of FIG. 4b.
Figure 4C:
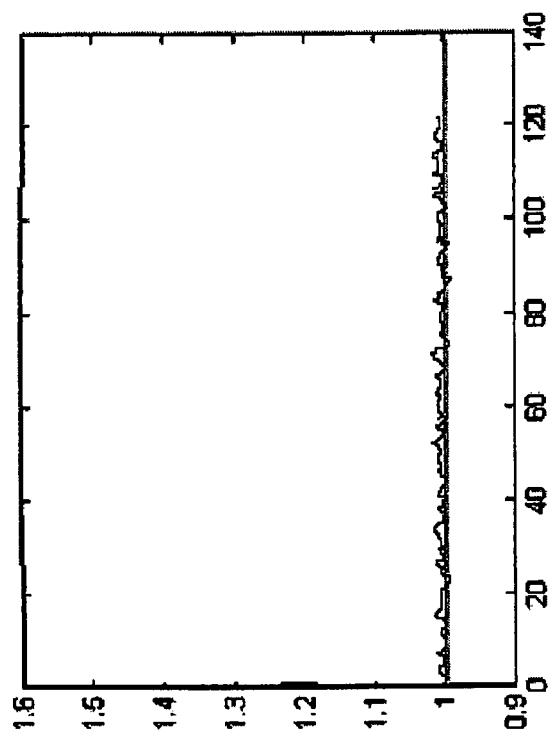
FIG. 4c is a plot of a T2 distribution curve corresponding to the noisy echo train from FIG. 3 using an independent component analysis (ICA) in accordance with one embodiment of the invention.
Figure 4F:
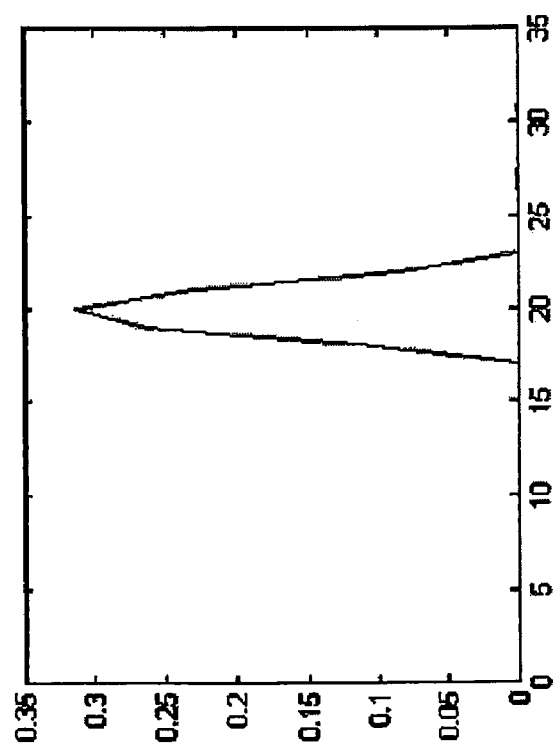
FIG. 4f is a plot of porosity characteristics corresponding to the T2 distribution of FIG. 4c, and reflecting application of an embodiment of the invention.

The porosity evaluations for the three cases of spectral component (T2) distributions (FIGS. 4a, 4b, and 4c) are shown in FIGS. 4d, 4e, and 4f, respectively. Notably, the noisy distribution of FIG. 4b results in a porosity evaluation as shown in FIG. 4e. There are significant and unmistakable differences between the prior art porosity evaluation of FIG. 4e and that of the noiseless (ideal) case, shown in FIG. 4d (FIG. 4d corresponding to prior art methodologies for deriving porosity profiles as applied to the noisy distribution 32).

On the other hand, FIG. 4f shows the porosity estimate for noisy T2 spectral component distribution 32 and T2 distribution 4c, as processed in accordance with the present teachings. Clearly, the porosity estimate of FIG. 4f more closely conforms to the "ideal" case of FIG. 4d than does the porosity estimate of FIG. 4e The ICA-BSS denoising thus is shown to significantly reduce the noise level in the porosity measurements, and practically eliminates the short T2 components resulting from prior art methodologies.

Those of ordinary skill in the art will be aware that T2 distributions represent the distribution of fluids in the pore space of an exploration region. Therefore, T2 distributions can have contributions from many fluid/material compositions and states of matter explored using NMR techniques. These compositions or states include, without limitation, clay-bound water (CBW), capillary bound water (BVI), movable water (MBWM), hydrocarbons (oil and gas), or oil-based mud filtrate (OBMfil).

By applying the ICA-based NMR analysis in accordance with the present disclosure on the T2 spectral component distributions at a certain depth interval, it is possible to extract the independent components (ICs) of T2 distributions. These IC-T2 distributions are not necessarily the components of the individual fluids in the formation, but the basic ones or source signals, which yield the calculated T2 distribution logs by the ICA approach.

Figure 5:
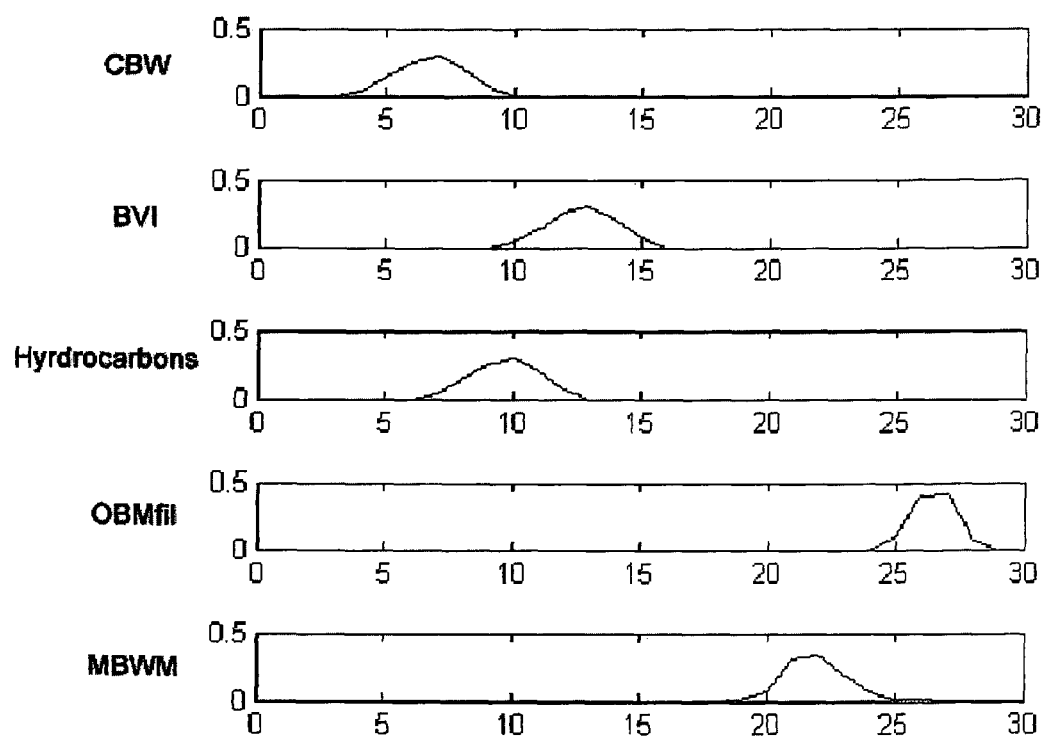
FIG. 5 comprises aligned plots of the relative presence of various fluid types versus a bin number correlative to a T2 distribution plot.
Figure 6:
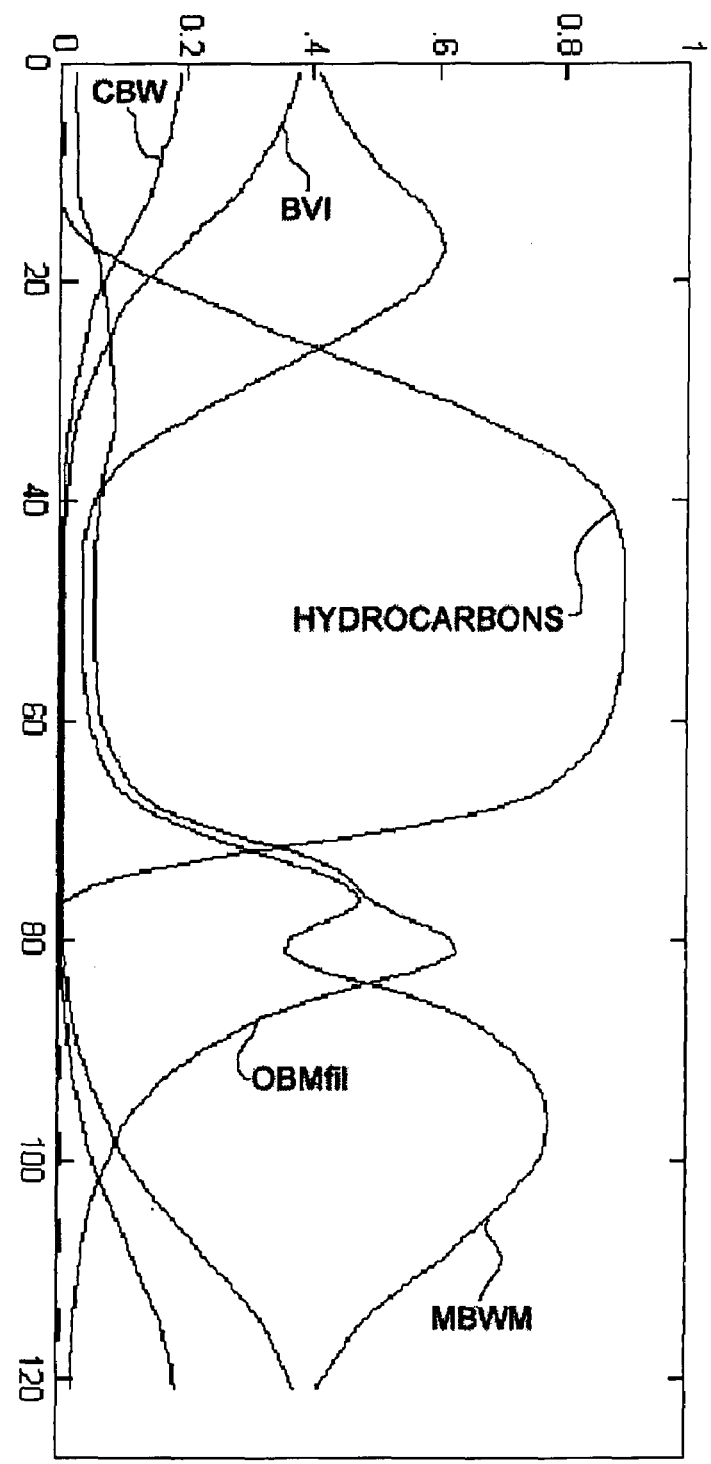
FIG. 6 is a plot of fluid saturation profiles for various fluids as identified therein and in accordance with an example of the invention.

Thus, in accordance with one aspect of the invention, the water and hydrocarbon saturations in a region can be calculated as follows:

First it is preferable to establish or define a correlation between the individual T2"bins" and the particular porosity characteristics and/or compositions that they represent. FIG. 5 shows a plurality (namely, thirty (30)) "bins" along the horizontal axis and the corresponding characteristic (correlative) T2 distributions for various fluids, namely clay-bound water (CBW), capillary-bound water (BVI), hydrocarbons (oil and gas), oil-based mud filtrate (OBMfil), and movable water (MBWM). The fluids' respective saturation profiles in depth (realizations) are plotted in FIG. 6. The echo trains were generated for the purposes of the illustrative embodiment, for TE=0.6 msec, and zero GTE (field gradient (G) times echo time (TE). Hence, as would be appreciated by those of ordinary skill in the art, no diffusion effects are taken into account in this illustrative case. It is apparent however, that this does not detract from the completeness of the present disclosure, inasmuch as the present invention may be practiced with or without additional techniques commonly employed in the field. That is, diffusion effects may or may not be taken into account in the course of practicing the present invention.

The T2 distributions of movable water (MBWM in FIG. 5) are generated using a pore space model such as the approach proposed in U.S. Pat. No. 7,257,490 to Georgi et al, entitled "Pore-Scale Geometric Models for Interpretation of Downhole Formation Evaluation Data," ("Georgi et al."), which patent is commonly assigned to the assignee of the present invention and which is hereby incorporated by reference herein in its entirety. The invasion profile may be determined by a linear weighting with the inverse of the shale volume. The hydrocarbon saturation may then be determined using various known methodologies, including those involving the Simandoux equation, $$\frac{1}{Rt} = \frac{\Phi^m Sw^n}{aRw} + \frac{VshSw}{Rsh}$$

where Rt is the formation resistivity, Rw is the formation water resistivity, Rsh is the shale resistivity, $\Phi$ is the porosity, a, m, and n are the Archie equation constants, Vsh is the fraction of shale, and Sw is the water saturation.

Figure 7:
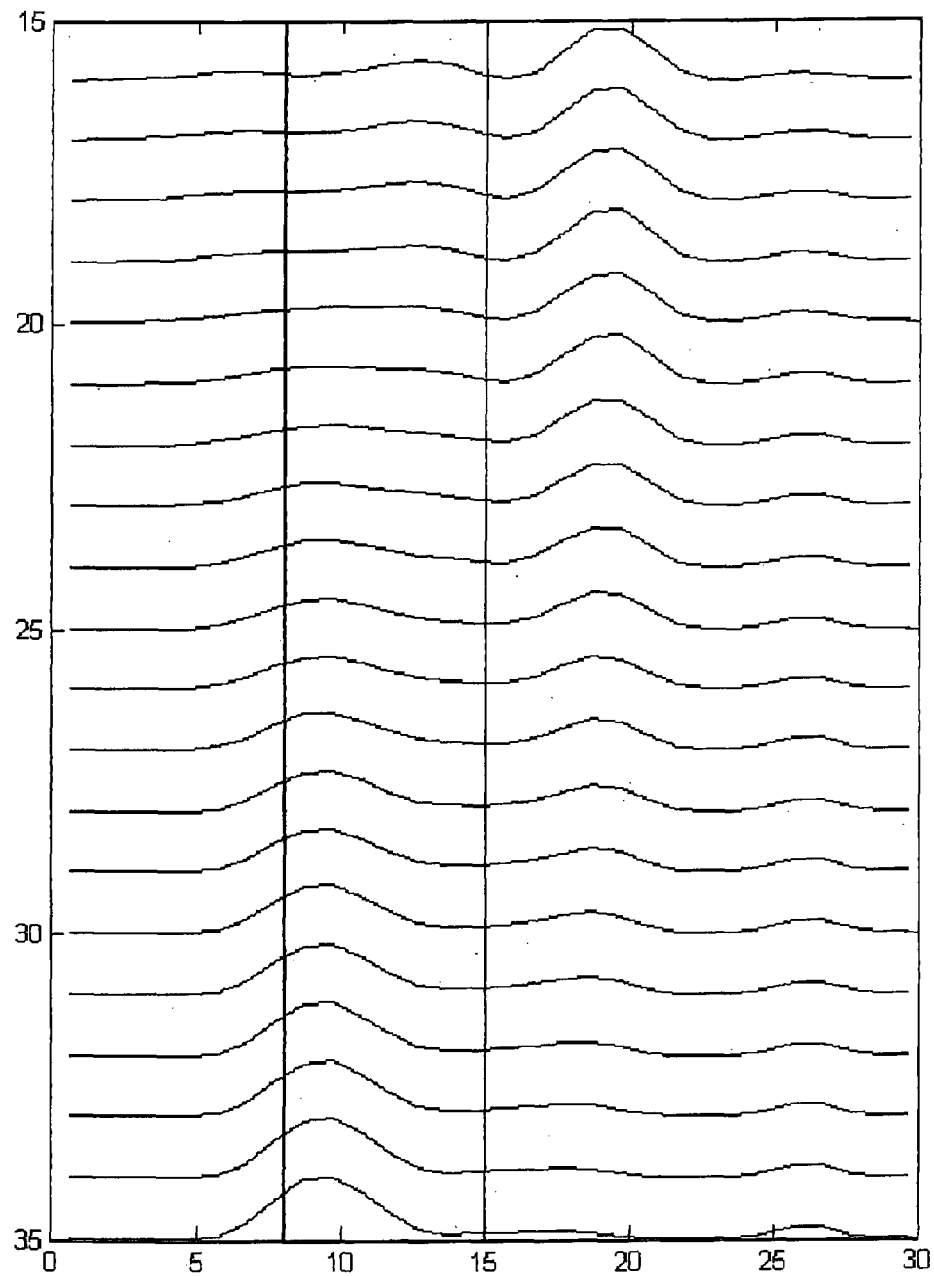
FIG. 7 shows T2 distributions generated for a range of depths in the example embodiment.
Figure 8:
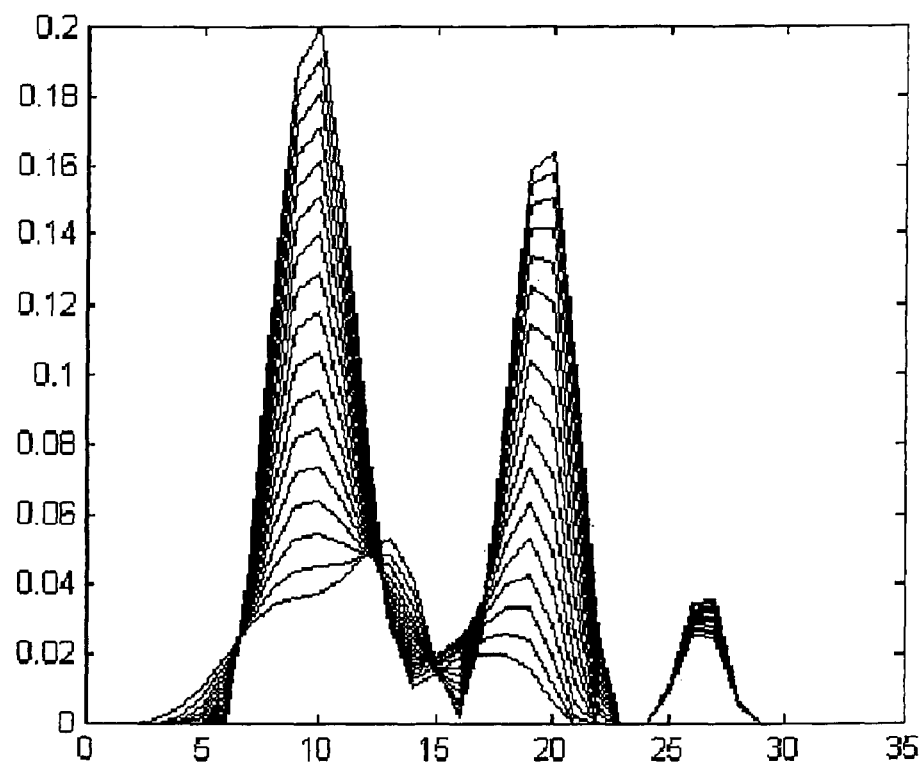
FIG. 8 shows T2 distributions generated for a range of depths in the example embodiment superimposed upon on another.

FIG. 7 shows the T2 distributions generated for the depth levels between 16 and 35. FIG. 8 shows essentially the same information, but overlapping all of the T2 distributions. The collective prominent features of the curves of FIG. 8 clearly show features of the T2 distributions centered at approximately bin numbers 10, 20, and 27.

Figure 9A:
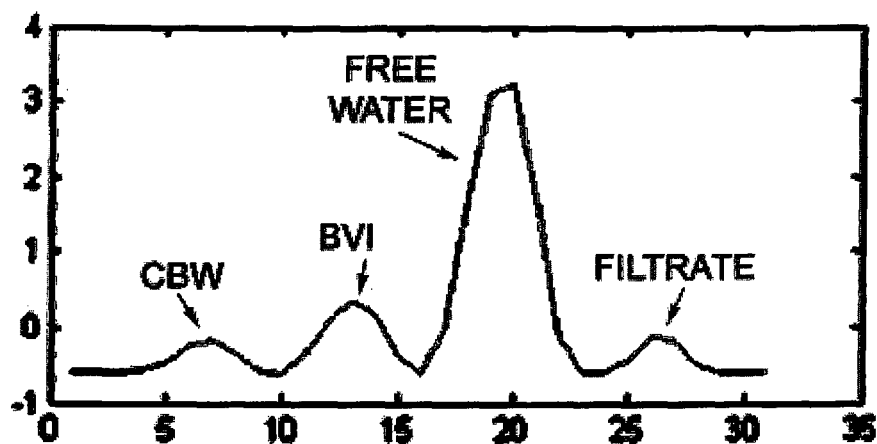
FIG. 9 is plot of T2 distributions revealing individually-identifiable contributions from various fluid categories in accordance with an ICA algorithm in accordance with the present invention.
Figure 9B:
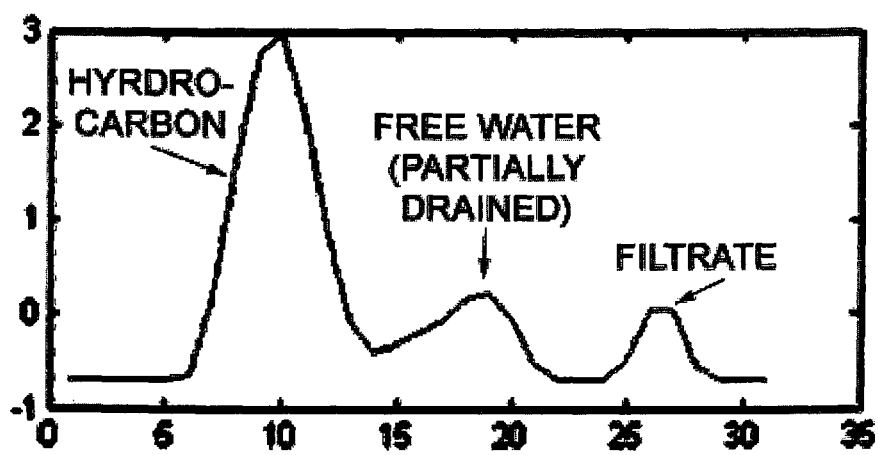

In accordance with one aspect of the invention, the very same result—and in most cases an even more detailed result—can be obtained through application of the independent component analysis algorithm in accordance with the presently disclosed embodiment of the invention, as applied to the exact same data. This is shown in FIGS. 9a and 9b, which present the independent components obtained from two different ICA algorithms. Those of ordinary skill will be familiar with various algorithmic alternatives for ICA, such as, for example, that embodied in the commercially available software FastICA, developed in part at the University of Helsinki and publically/commercially available at http://www.cis.hut.fi/proiects/ica/fastica/code/dlcode.shtml. FastICA implements a fixed point iteration scheme for independent component analysis. Another ICA approach is proposed in Stogbauer et al., Mutual Information Based Least Dependent Component Analysis," *Phys Rev. E* 70(6) 066123, 2004.

For example, the T2 distribution curve in FIG. 9a has a prominent independent component feature centered at approximately bin number 20 that is correlative to the presence of free water in the region being analyzed. Similarly, the T2 distribution curve in FIG. 9b has an observable independent component feature centered at approximately bin number 10 correlative to the presence of hydrocarbons in the exploration region.

In accordance with a further aspect of the invention, the saturation of any fluid, including hydrocarbons, can be derived by selecting its T2 bin window in the ICA T2 distribution plot(s) generated in accordance with the present disclosure and generating a saturation evaluation curve. In the simplest implementation the saturation curve is generated by multiplying a T2 distribution by an associated matrix A determined as described in detail above, namely, x=A*s.

Those of ordinary skill in the art will further appreciate that the T2 distribution curves derived in accordance with the present invention may be further processed to characterize other properties of the exploration region, for example, by applying the well-known Timur-Coates permeability formulation and/or any of a number of other well-known interpretation models and parameters thereof.

In accordance with still a further feature of the invention, it is contemplated that independent component analysis techniques may be applied to the underlying time domain data prior to its transformation to a T2 distribution. This advantageously results in "de-noising" of the signal, leading to more precise and accurate results following analysis of the T2 distribution.

From the foregoing disclosure, it should be apparent that a system and method for nuclear magnetic resonance analysis based on a blind source separation-based methodology has been disclosed. Those of ordinary skill in the art will recognize that the methodology of the present invention may be advantageously practiced in conjunction with any one of a multitude of known NMR devices, including, for example, the device disclosed in U.S. Pat. No. 6,247,542 to Kruspe et al., the Kruspe '542 patent being hereby incorporated by reference herein in its entirety. U.S. Pat. No. 7,193,414 to Kruspe et al. is another example of prior art teachings of NMR techniques and tools/devices with which the present invention may be advantageously practiced. The Kruspe '414 patent is also hereby incorporated by reference herein in its entirety.

Although a specific embodiment of the invention as well as possible variants and alternatives thereof have been described and/or suggested herein, it is to be understood that the present disclosure is intended to teach, suggest, and illustrate various features and aspects of the invention, but is not intended to be limiting with respect to the scope of the invention, as defined exclusively in and by the claims, which follow.

Indeed, it is contemplated and to be explicitly understood that various substitutions, alterations, and/or modifications, including but not limited to any such implementation variants and options as may have been specifically noted or suggested herein, including inclusion of technological enhancements to any particular method step or system component discovered or developed subsequent to the date of this disclosure, may be made to the disclosed embodiment of the invention without necessarily departing from the technical and legal scope of the invention as defined in the following claims.

What is claimed is:

1. A method of evaluating a subsurface region, the method comprising:
   using a receiver on a logging tool conveyed in a borehole for receiving a plurality of signals, each of the plurality of signals comprising-an echo train from a different depth of the logging tool in the borehole; and
   using a processor for:
      (i) deriving a transformation matrix using a blind-source separation (BSS)-based independent component analysis (ICA) on said plurality of signals;
      (ii) multiplying at least one of the plurality of signals by the transformation matrix to give an estimated T2 distribution for the at least one of the plurality of signals; and
      (iii) identifying at least one feature of the estimated T2 distribution known a priori to be correlative to a particular composition of said subsurface region.

2. The method of claim 1, wherein the at least one feature is correlative to the presence of hydrocarbons in said subsurface region.

3. The method of claim 1, further comprising applying an ICA on each of the plurality of signals prior to multiplying by the transformation function, thereby reducing noise in a resultant spectral component distribution.

4. A system configured to evaluate a subsurface region comprising:
   a receiver on a logging tool conveyed in a borehole and configured to receive a plurality of signals, each of the plurality of signals comprising an echo train from a different depth of the logging tool in the borehole; and
   a processor configured to:
      (i) derive a transformation matrix using a blind source separation (BSS)-based independent component analysis (ICA) of the plurality of signals;
      (ii) multiply at least one of the plurality of signals by the transformation matrix to give an estimated T2 distribution for the at least one of the plurality of signals; and
      (iii) identify at least one feature of the estimated T2 distribution known a priori to be correlative to a particular composition of the subsurface region.

5. The system of claim 4, wherein the at least one feature is correlative to the presence of hydrocarbons in said exploration region.

6. The system of claim 4, wherein the processor is further configured to apply an ICA each of the priority of signals prior to multiplying by the transformation function, thereby reducing noise in a resultant spectral component distribution.

* * * * *